(12) United States Patent
Johnson et al.

(10) Patent No.: US 7,040,143 B2
(45) Date of Patent: May 9, 2006

(54) METHOD AND APPARATUS FOR TESTING SURFACE CHARACTERISTICS OF A MATERIAL

(75) Inventors: David L. Johnson, Clinton, UT (US); Karl D. Kersker, Pleasant View, UT (US); David E. Richardson, Brigham City, UT (US); Troy C. Stratton, Brigham City, UT (US)

(73) Assignee: Alliant Techsystems Inc., Edina, MN (US)

( * ) Notice: Subject to any disclaimer, the term of this patent is extended or adjusted under 35 U.S.C. 154(b) by 36 days.

(21) Appl. No.: 10/651,311

(22) Filed: Aug. 28, 2003

(65) Prior Publication Data

US 2005/0044960 A1 Mar. 3, 2005

(51) Int. Cl.
*G01M 3/34* (2006.01)

(52) U.S. Cl. ........................................ 73/49.3
(58) Field of Classification Search ............... 73/37, 73/49.3, 37.9, 40, 49.2
See application file for complete search history.

(56) References Cited

U.S. PATENT DOCUMENTS

| | | | | |
|---|---|---|---|---|
| 3,693,424 A | | 9/1972 | Wagle | |
| 3,771,649 A | * | 11/1973 | Strauss | 209/3.1 |
| 3,934,464 A | | 1/1976 | McCauley | |
| 4,459,843 A | * | 7/1984 | Durham | 73/37 |
| 4,733,973 A | * | 3/1988 | Machak et al. | 374/5 |
| 5,001,935 A | | 3/1991 | Tekkanat et al. | |
| 5,265,464 A | | 11/1993 | Caron et al. | |
| 5,345,829 A | | 9/1994 | Yamauchi et al. | |
| 5,546,789 A | * | 8/1996 | Balke et al. | 73/40 |
| 5,571,955 A | | 11/1996 | Beavers et al. | |

* cited by examiner

*Primary Examiner*—Max Noori
(74) *Attorney, Agent, or Firm*—TraskBritt (57) ABSTRACT

A method, apparatus and system for testing characteristics of a material sample is provided. The system includes an apparatus configured to house the material test sample while defining a sealed volume against a surface of the material test sample. A source of pressurized fluid is in communication with, and configured to pressurize, the sealed volume. A load applying apparatus is configured to apply a defined load to the material sample while the sealed volume is monitored for leakage of the pressurized fluid. Thus, the inducement of surface defects such as microcracking and crazing may be detected and their effects analyzed for a given material. The material test samples may include laminar structures formed of, for example, carbon cloth phenolic, glass cloth phenolic, silica cloth phenolic materials or carbon-carbon materials. In one embodiment the system may be configured to analyze the material test sample while an across-ply loading is applied thereto.

46 Claims, 11 Drawing Sheets

# METHOD AND APPARATUS FOR TESTING SURFACE CHARACTERISTICS OF A MATERIAL

STATEMENT OF GOVERNMENT RIGHTS

The United States Government has certain rights in the present invention pursuant to Contract No. NAS8-897238 between the National Aeronautics and Space Administration (NASA) and Thiokol Corporation (now Alliant Techsystems Inc.).

BACKGROUND OF THE INVENTION

1. Field of the Invention

The present invention relates generally to an apparatus and method of testing materials and, more particularly, to the testing of materials to determine surface characteristics and the effect thereof relative to the formation of a seal against such a surface.

2. State of the Art

In order to properly engineer or design a structure, mechanism, device or other component, it is necessary to have an understanding not only of a specific technological discipline (e.g., mechanical or electrical engineering) but also of the properties and characteristics of various materials which are available for construction of the resulting device. For example, it is desirable to understand strength related properties, such as the modulus of elasticity, yield strength, tensile strength and ductility for a given metal or alloy before utilizing such a material to form a structural member (e.g., a beam, truss, frame, shaft, etc.). Similarly, it is important to understand a material's electrical properties, such as its coefficient of conductivity (or resistivity), in designing, for example, an integrated circuit package. Other conventional material properties and characteristics which are often utilized in the engineering and designing of a particular device or component include, for example, thermal conductivity, coefficient of thermal expansion, density, as well as numerous other properties and characteristics.

Often the device being designed and manufactured is a complex structure meaning that multiple materials are being used and multiple components are being fitted together in a specific arrangement in order to achieve a desired result. Thus, it becomes even more important to understand the properties and characteristics of materials, not simply in isolation, but also in terms of compatibility with other materials as well as in terms of how the materials might react in potential situations not previously considered or analyzed.

Certain properties or characteristics of a given material may be known as a result of prior use or testing. For example, the exemplary material properties set forth above are often known, and often listed in standardized tables, for various materials including, for example, common metallic or alloyed materials. However, even having a basic understanding of the properties and characteristics of a given material, it can still be difficult to predict how a particular material may perform in a new application or environment. This may be particularly true in the case where multiple materials are being combined such as is the case with composite materials. Similarly, if a failure occurs in a device or assembly which includes several components and is formed of multiple materials, it can be difficult to determine which component or components and/or, which material or materials, ultimately led to the failure.

For example, if a seal, which is disposed between two components, fails to prevent fluid flow between the two components, it may not be immediately apparent whether the failure is due to an improper design or configuration of the seal or some other factor. In fact, oftentimes investigation must be made into the possibility of such other factors in order to more fully understand why a particular component or material performed in a particular manner.

In one particular example, as shall be discussed in further detail below, the failure of a seal element to prevent fluid flow between two adjacent components led to investigations regarding, among other things, advanced material properties and characteristics such as the occurrence of microcracking and/or crazing within various materials and the effect of such phenomena on the ability to of a material's surface to form an appropriate seal when abutted by the sealing element.

In conducting such investigations it was determined that existing testing equipment and methods were not adequate to provide the desired analysis. Thus, it was determined that it would be advantageous to provide a method and apparatus for testing materials to determine certain properties of materials, such as microcracking and crazing, and the effect of such phenomena under various circumstances.

BRIEF SUMMARY OF THE INVENTION

In accordance with one aspect of the invention a method of testing the surface characteristics of a material is provided. The method includes providing a body comprising the material which is to be tested. A sealed volume is defined, wherein a portion of the sealed volume includes a surface of the body. A pressurized fluid is supplied to the sealed volume and load is applied to the body. The sealed volume is then monitored for indications of a loss of the pressurized fluid. For example, the pressure of the fluid within the sealed volume may be monitored for a change therein while the load applied to the body is varied in some manner.

In accordance with another aspect of the present invention, a testing apparatus is provided. The apparatus includes a first support member, a second support member and a plurality of spacers disposed between the first support member and second support member. The spacers are located and configured to define a volume for receipt of a material test sample between the first support member and second support member. A circuitous seal member is located and configured to be disposed against a surface of the second support member and a surface of the material test sample. One or more shims may be used in conjunction with the spacers to control the percent squeeze applied to the seal member. A port is located and configured to be in fluid communication with an interior area defined by the circuitous seal member.

In accordance with yet another aspect of the present invention, a system is provided. The system includes a test fixture having a first support member, a second support member and a plurality of spacers disposed between the first support member and second support member and defining a volume for receipt of a material test sample between the first support member and second support member. A seal member is disposed against a surface of the second support member and against a surface of the material test sample thereby forming a sealed volume therebetween. A source of pressurized fluid is in fluid communication with the sealed volume and a load applying apparatus is configured to apply a defined load to the material test sample.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
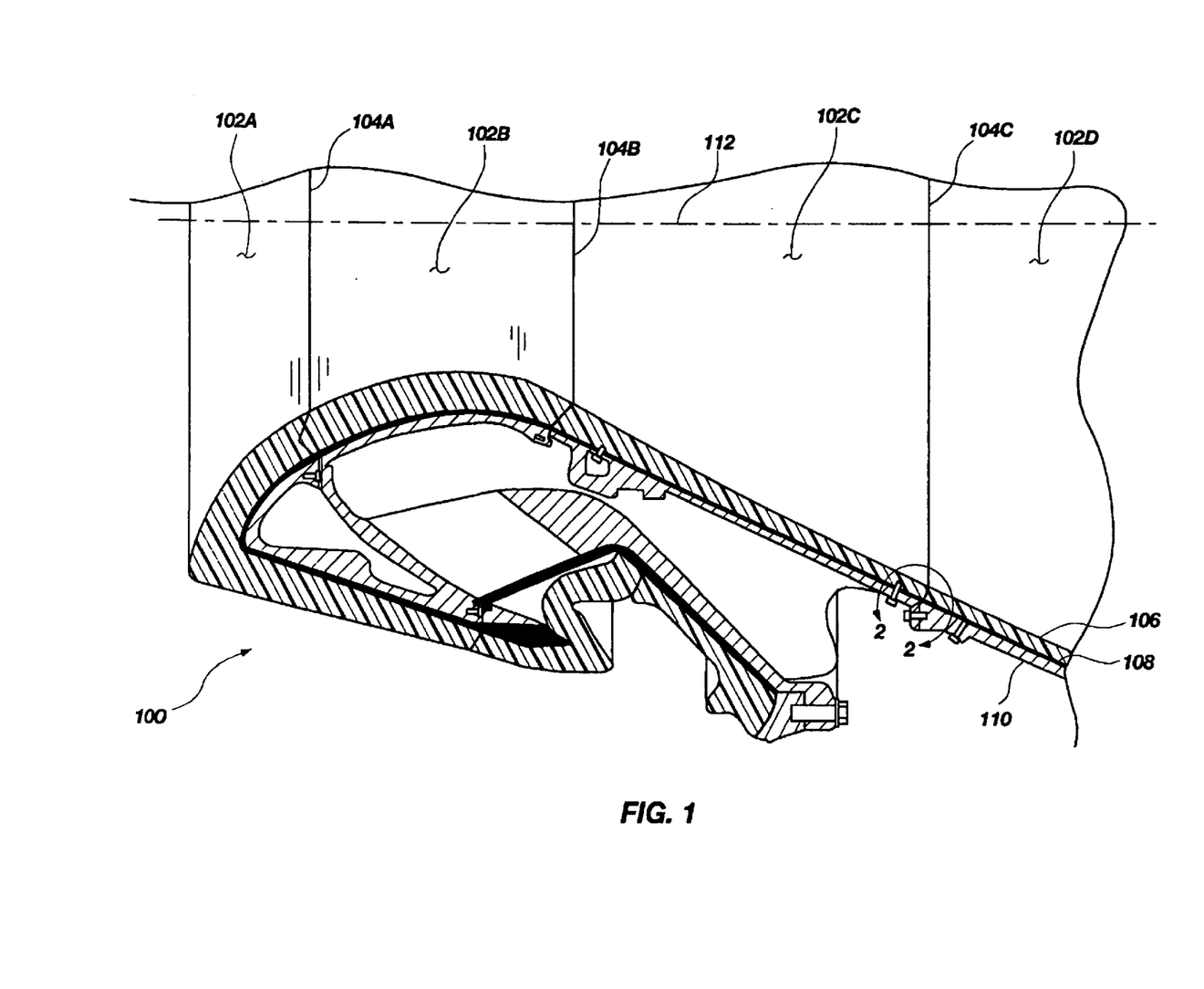
FIG. 1 is a partial cross-sectional view of a prior art nozzle used with a rocket motor assembly.

Referring to FIG. 1, a partial cross-sectional view is shown of a nozzle 100 which may be associated with, for example, a solid rocket motor. The nozzle 100 may be formed as individual sections 102A–102D which are fitted to one another and respectively define joints 104A–104C between adjacent sections 102A–102D. For example, section 102A may be what is referred to as an inlet ring, section 102B may be referred to as a throat ring, section 102C may be referred to as a forward exit cone, and section 102D may be referred to as an aft exit cone as will be appreciated by those of ordinary skill in the art. The nozzle 100 may include other sections but such additional sections are not shown in FIG. 1 for purposes of convenience and clarity.

Each section 102A–102D may be formed of a plurality of materials including, for example, an inner layer 106 of carbon cloth phenolic (CCP) material, an intermediate layer 108 of glass cloth phenolic (GCP) material or silica cloth phenolic, and an outer metallic skin or housing 110 such as aluminum. The inner layer 106 of CCP material acts as an ablative material when high temperature, expanding gases are flowing through the nozzle 100 upon combustion of the fuel of an associated rocket motor. The intermediate layer 108 of GCP may act as a structural component, a corrosion barrier and as thermal insulation disposed between the hot gases flowing through the nozzle 100 and the structural skin or housing 110 of the nozzle 100. The inner layer 106 and the intermediate layer 108 may each be formed by wrapping a plurality of plies of desired material about a mandrel.

For example, the inner layer 106 may be formed by wrapping a plurality CCP plies about a mandrel such that each ply is substantially oriented at a defined angle (e.g., an acute angle) relative to the longitudinal axis 112 of the nozzle 100. The intermediate layer 108 may be formed by wrapping a plurality of plies about the already formed inner layer 106 in what may be termed a "baseball wrap" configuration such that a portion of each newly disposed ply overlaps a portion of each previously disposed ply. Although it may contain multiple layers to form a laminar structure, the resulting structure thus resembles the tape which is wrapped about the handle or grip portion of a baseball bat.

As noted above, the integration of multiple materials (e.g., CCP, GCP and metals or metal alloys) presents numerous design issues and may make it difficult to determine the source of a component failure. Additionally, the fact that a component is formed of a composite material such as CCP and GCP may further complicate the analysis of a given structure or component in terms of its performance and/or failure.

Figure 2:
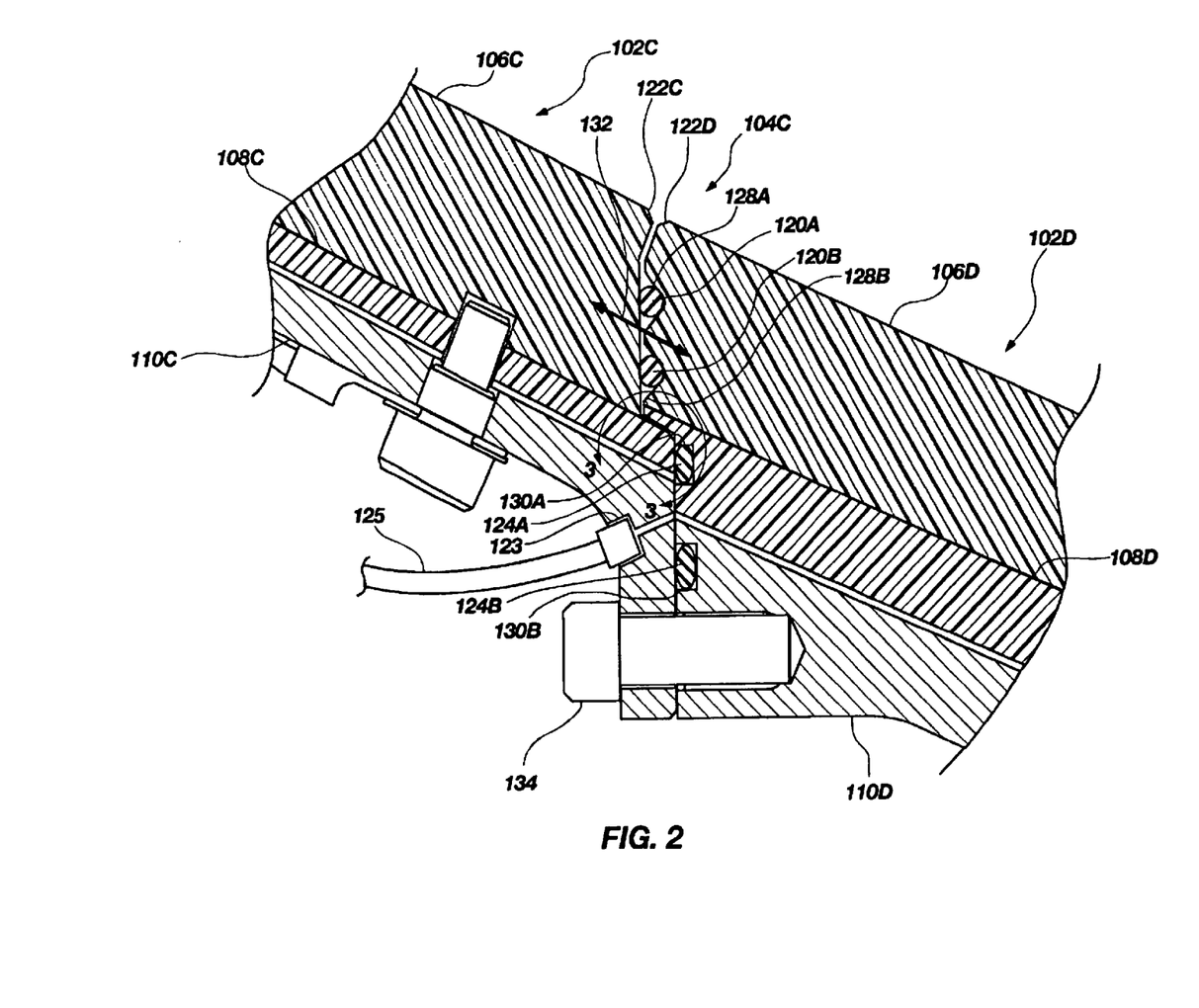
FIG. 2 is a cross-sectional view of a joint formed in the nozzle of FIG. 1.

For example, referring to FIG. 2, a joint 104C between two sections 102C and 102D (e.g., the forward and aft exit cones respectively) is shown in further detail. The joint 104C is formed by the adjacent sections 102C and 102D being fitted together with a set of thermal barriers 120A and 120B formed between the respective circumferential edges 122C and 122D of each section's inner layer 106C and 106D. The joint 104C also includes a set of seals including one seal 124A being formed between the respective circumferential edges 122C and 122D of each section's intermediate layer 108C and 108D and another seal 124B being formed between the respective circumferential edges 122C and 122D of each section's outer skin or housing 110C and 110D. The set of thermal barriers 120A and 120B may include, for example, carbon fiber ropes (CFR) each disposed in circumferential channel or groove 128A and 128B. The set of seals 124A and 124B may include, for example, o-rings formed of a suitable elastomer material, such as nitrile rubber, disposed in circumferential channels or grooves 130A and 130B.

In testing a joint similar to joint 104C, a test port 123 may also be provided to monitor gases flowing through the joint 104C. The test port 123 may be coupled with a conduit member 125 or other structure to provide fluid pressure from a pressure source (not shown) for leak testing the seals 124A and 124B in a controlled environment. After the seals 124A and 124B have been tested, assuming that no leaks have been detected, a plug (not shown) may be inserted into test port 123 for the sealing thereof during in-flight use of the nozzle 100.

For example, on at least one occasion during a leak-check test of a joint such as joint 104C, test gases flowing through test port 123 were found to have leaked past the seal 120B. Investigation of the leaky seal revealed that, on this particular occasion, one of thermal barriers (e.g., thermal barrier 120B) was not properly seated within the associated groove 128B and, thus, became crushed between portions of the edges 122C and 122D of the two sections 102C and 102D. It is believed that the improper installation of at least one of the thermal barriers 120A and 120B (e.g., thermal barrier 120B) resulted in an unintended force applied between the inner layers 106C and 106D of the two sections 102C and 102D, as indicated by directional arrow 132, upon the tightening of fastener member 134.

Figure 3:
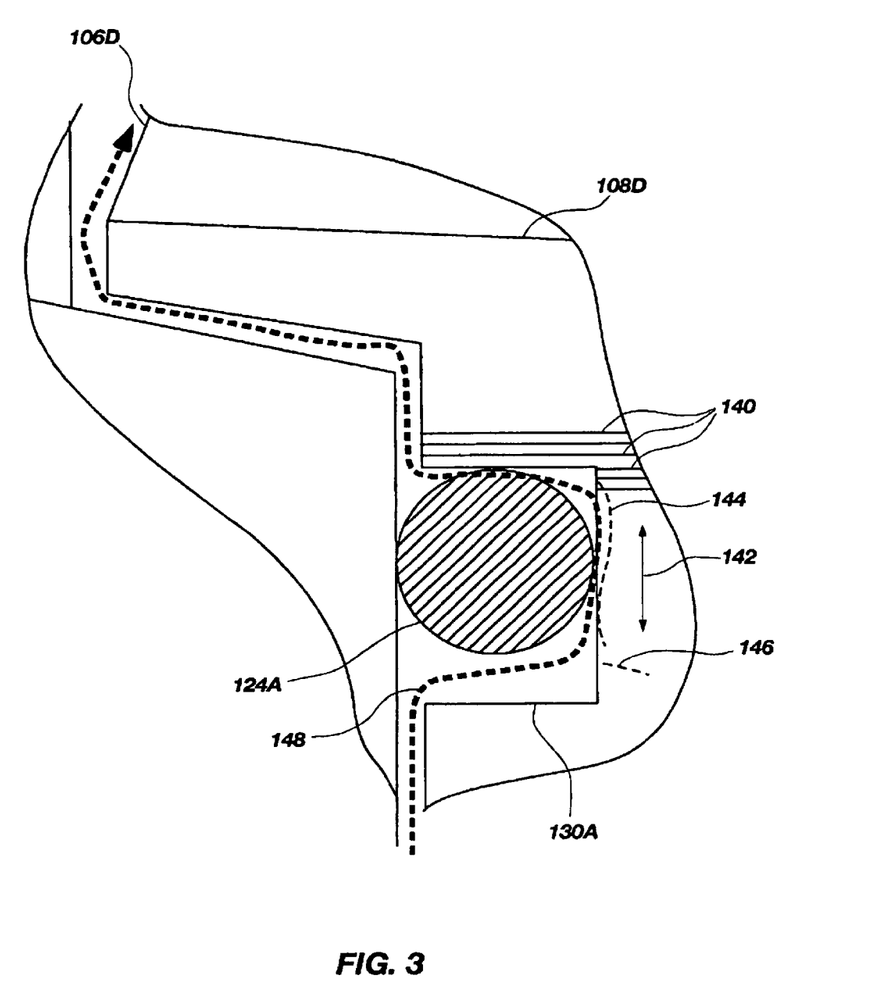
FIG. 3 is an enlarged view of a portion of the joint of FIG. 2.

Referring briefly to FIG. 3, which shows an enlarged view of a portion of the joint 104C shown in FIG. 2, one theory regarding the failure of the joint 104C suggested that the unintended force applied between the two sections 102C and 102D resulted in a state of across-ply tension within the groove 130A. In other words, the groove 130A is formed within the intermediate layer 108D having plies 140 (only some of which plies 140 are shown for sake of clarity), stacked or overlapping in a substantially radially laminar manner. The unintended force between the two sections resulting from the combination of the tightened fastener member 134 and the pinched thermal barrier (e.g., thermal barrier 120B) induced a pulling or tensile force in a direction indicated by directional arrow 142. It is believed that the across-ply tensile force induced microcracking and/or crazing within the resin or matrix material of the intermediate layer 108D. The microcracks and crazing, indicated generally by dashed lines 144 and 146, are believed to have propagated along the surface of the channel 130A. The surface defects or discontinuities produced by such microcracking and crazing are believed to have provided a flow path around the seal 124A, through the defects (e.g., those indicated by dashed lines 144 and 146), and through the joint 104C as indicated by dashed line 148.

In order to more extensively analyze the effects of potential microcracking and crazing on a joint/seal arrangement, such as may be induced by an across-ply tensile force, a testing apparatus and method was devised as described hereinbelow.

Figure 4:
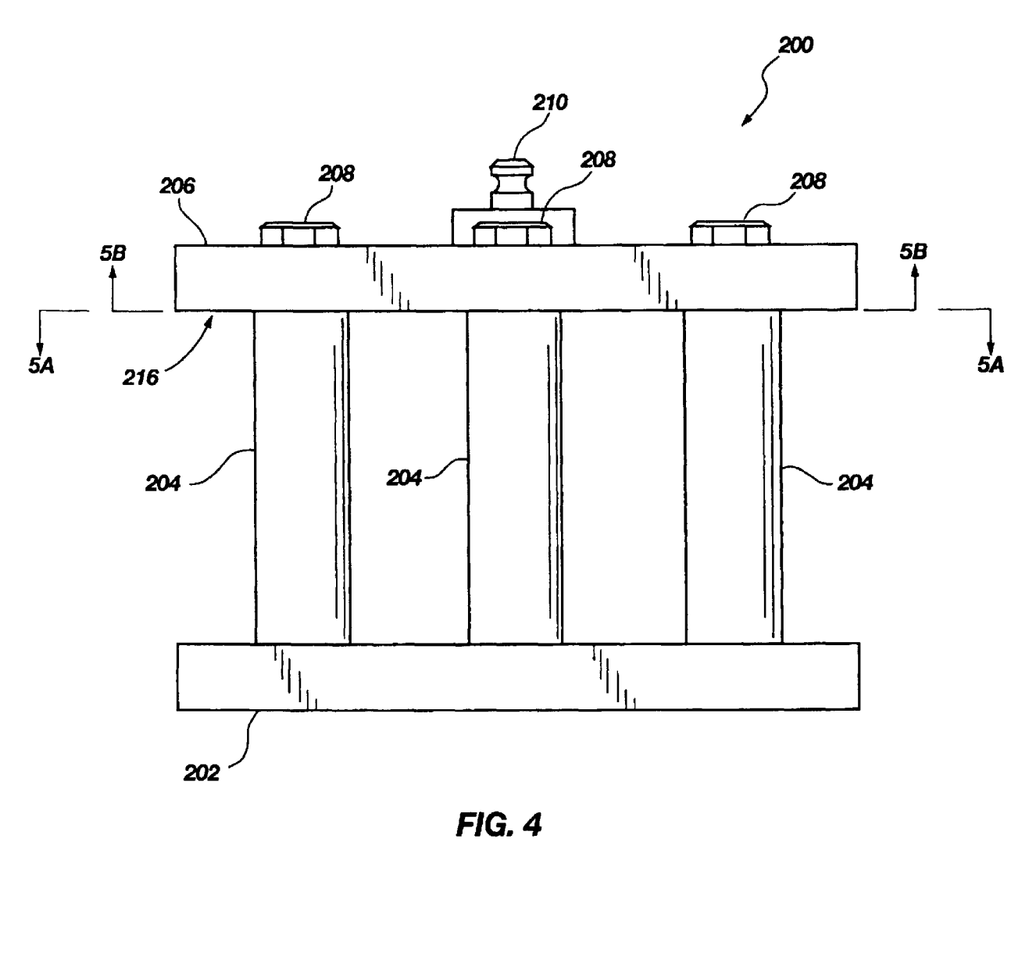
FIG. 4 is a side view of an assembled testing apparatus in accordance with an embodiment of the present invention.

Referring to FIG. 4, a testing fixture, also referred to herein as a testing apparatus 200, is shown in accordance with an embodiment of the present invention. The testing apparatus 200 includes a first support member, referred to herein as a base plate 202, a plurality of spacers 204 and a second support member, referred to herein as a top plate 206. A plurality of fasteners 208 are used to removably couple the base plate 202, the spacers 204 and top plate 206 to one another.

Figure 5A:
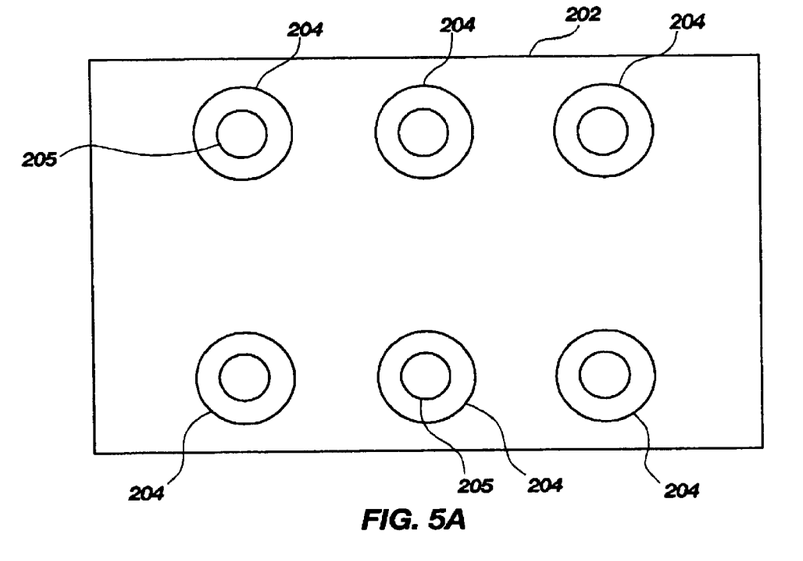
FIGS. 5A and 5B show plan views of various components of the testing apparatus of FIG. 4.
Figure 5B:
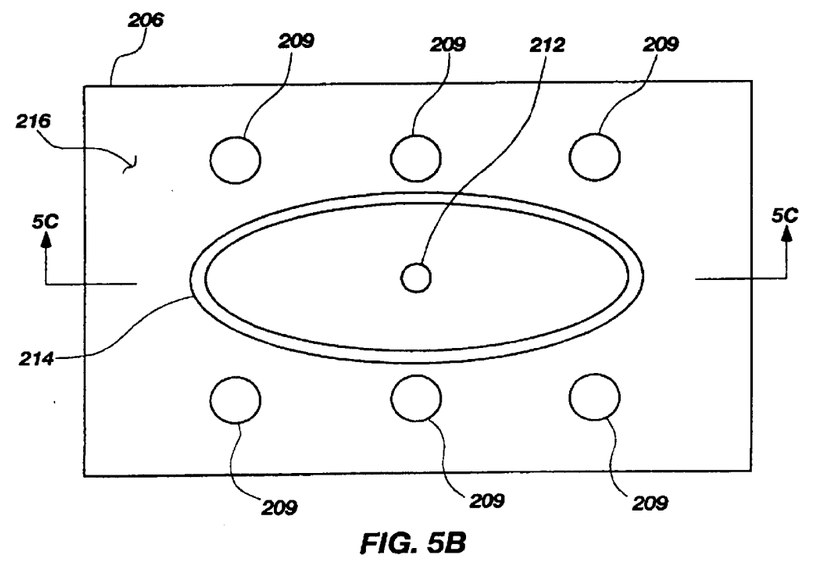

For example, referring to FIGS. 5A and 5B in conjunction with FIG. 4, in one embodiment a plurality of threaded holes may be formed in the base plate 202 such that the fasteners 208 may extend through corresponding holes in the top plate 206, through channels or passages 205 formed in the spacers 204 and threadably engage the base plate 202. In another embodiment, the spacers 204 may be more permanently coupled to the base plate 202 such as, for example, by welding, brazing, or adhesive bonding. In such a case, the spacers 204 may include internal threads such that the fasteners 208 extend through a plurality of holes 209 in the top plate 206 and threadably engage the spacers 204.

Figure 5C:
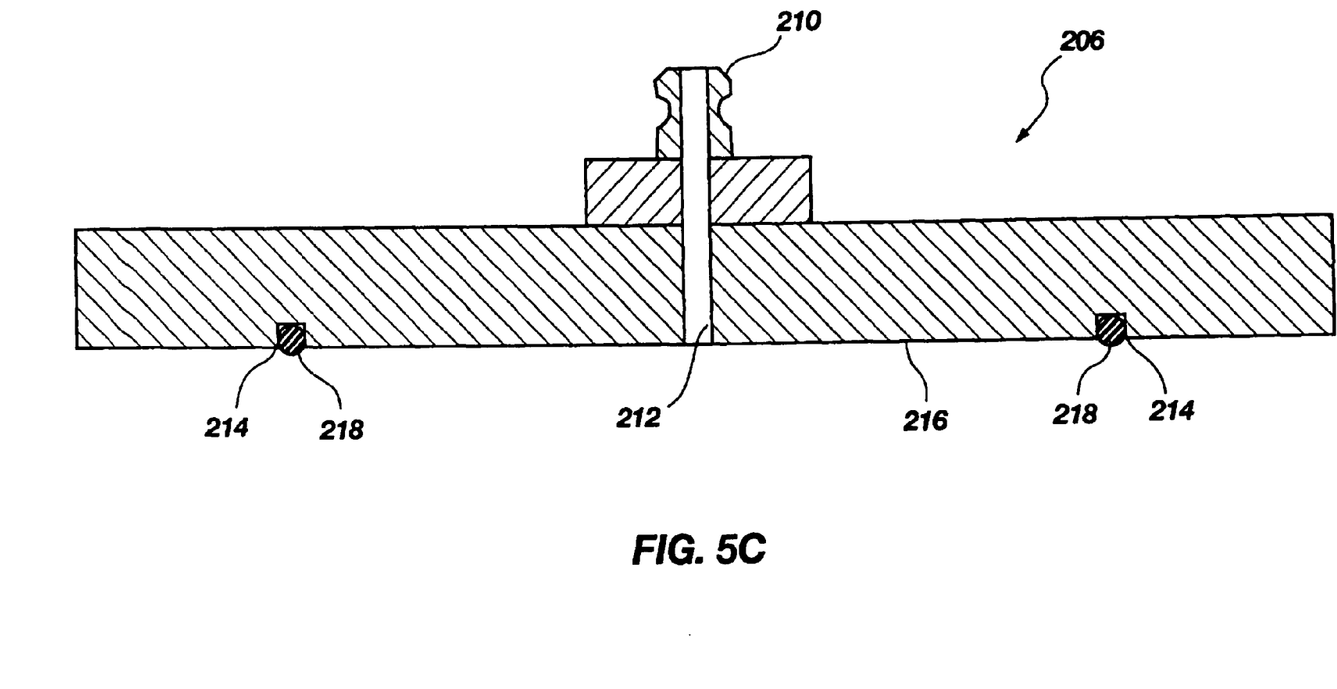
FIG. 5C is a cross-sectional view of the component shown in FIG. 5B.

A port 210 is coupled with the top plate and configured to be coupled with a fluid source (not shown in FIGS. 4, 5A or 5B). The port 210 is in fluid communication with a through hole or opening 212 formed in the top plate 206 to provide fluid communication from one side of the top plate 206 to the other. The top plate 206 further includes a circuitous groove 214 formed in a surface 216 thereof. As shown in FIG. 5C, The groove is configured to house an o-ring 218 or other seal member. The testing apparatus 200 is generally configured to house a test sample and, utilizing the o-ring 218, form a sealed pocket against a surface of the test sample and with the port 210 being in fluid communication with the sealed pocket as described in further detail below.

Figure 6:
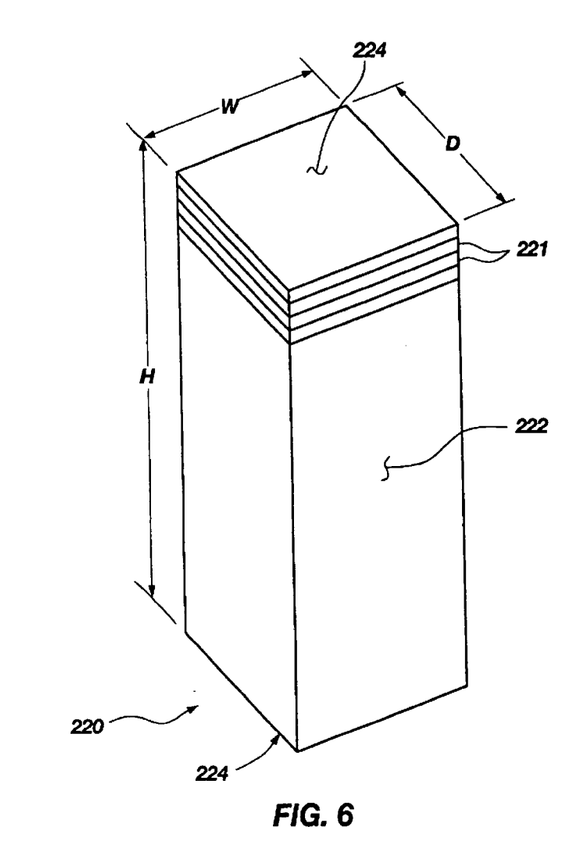
FIG. 6 is a perspective view of a material sample to be tested in accordance with an embodiment of the present invention.

An exemplary test sample 220, as shown in FIG. 6, may include a block of material formed to specific dimensions, surface finishes and tolerances. For example, a block may be formed of a plurality of plies 221 of CCP, GCP, SCP, carbon-carbon material (CC) or some other composite material disposed upon each other in a laminar manner (only a few of which plies 221 are shown for purposes of clarity). In one embodiment, the test sample 220 may exhibit a width W of approximately 1.7 inches, a depth D of approximately 1.7 inches and a height H of approximately 3.5 inches. The plies may be stacked such that each ply extends substantially across the sample's depth D and width W thereby exhibiting a laminar structure substantially transverse to its height H. At least one lateral surface 222 (e.g., a surface other than an end surface 224) may be machined, ground, polished or otherwise finished to exhibit a surface finish of approximately 63 Å Ra (angstroms, roughness average). It is noted that, while the exemplary embodiments described herein refer generally to composite materials, in other embodiments the test sample may be formed of a molded component including, for example, a molded epoxy resin, or any other resinous laminate material. Additionally, the test sample may exhibit other dimensions than the exemplary dimensions provided herein and, assuming a composite structure formed of a plurality of plies, the plies 221 may exhibit other angles of orientation relative to the end surfaces 224 and lateral surfaces 222 as may be desired.

Figure 7:
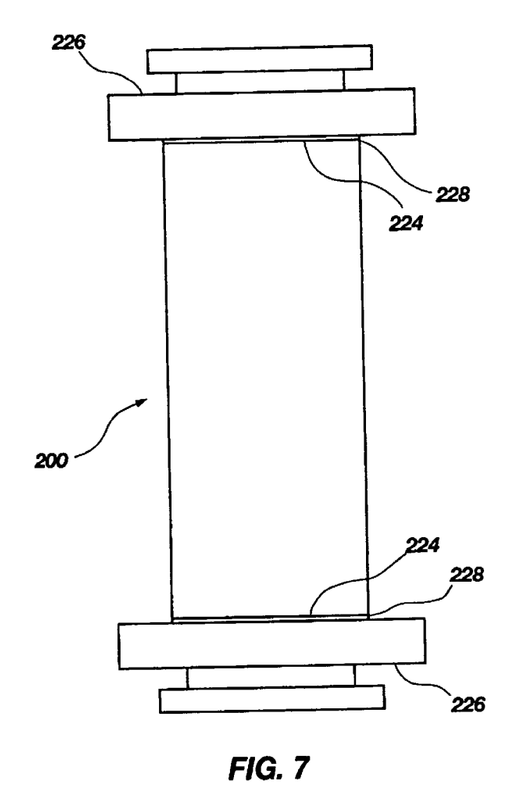
FIG. 7 is a side view of the material sample of FIG. 6 configured for testing in accordance with an embodiment of the present invention.

Referring to FIG. 7, the test sample 220 may have plates or other fixtures 226 coupled to the end surfaces 224 of the test sample 220. The fixtures 226 may be formed of a metal or metal alloy material such as, for example, aluminum. In one embodiment, the fixtures 226 may be bonded to the end surfaces 224 using an appropriate adhesive 228. For example, if the test sample 220 is formed as a CCP laminate structure, it may be desirable to bond the end surfaces 224 of the test sample to the fixtures 226 using a TIGA 321 epoxy adhesive which is commercially available from Resin Technology Group, LLC, of South Easton, Mass. As will be discussed in further detail below, the fixtures are configured to operatively engage with a load applying device so as to apply a force of a known magnitude and direction. For example, in one embodiment, the test sample 220 and fixtures 226 may be configured so that a load may be applied in a direction substantially perpendicular to the end surfaces 224 of the test sample 220 which, in the exemplary embodiment, provides an across-ply tensile loading to the test sample 220.

Figure 8:
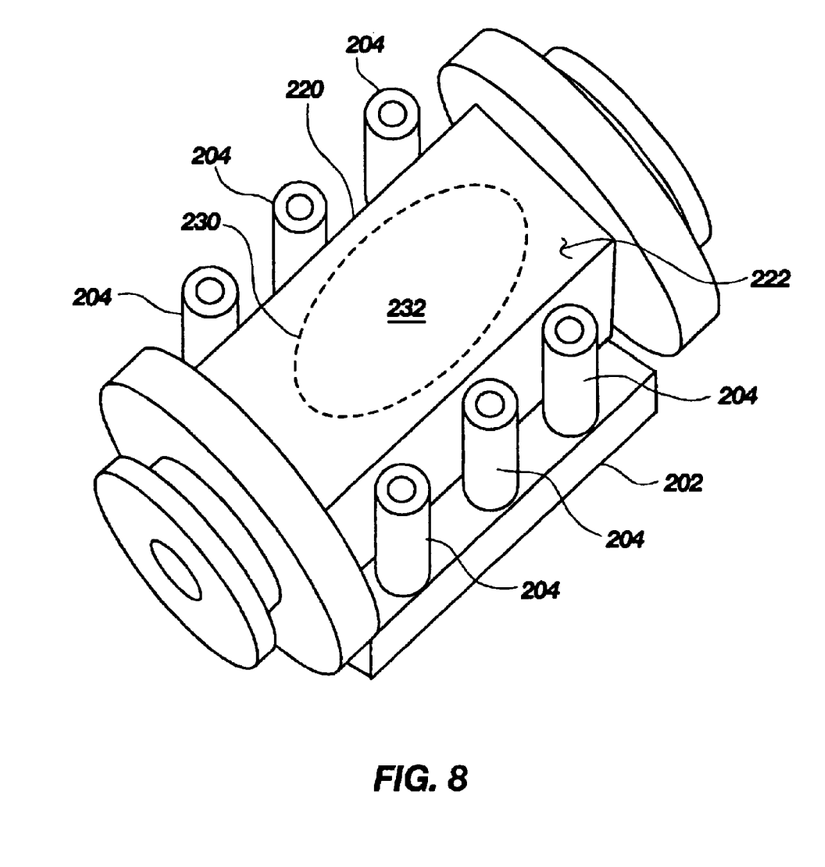
FIG. 8 is a perspective view of a material sample disposed in a portion of a testing apparatus in accordance with another embodiment of the present invention.

Referring to FIG. 8, in anticipation of undergoing a defined test procedure or routine, the test sample 220 is placed on the base plate 202 and the spacers 204 are positioned adjacent the test sample 220 along two opposing sides thereof. A dashed line 230 indicates the positioning of the o-ring 218 or other sealing member disposed in the groove 216 of the top plate 206 (see, e.g., FIG. 5C) relative to the test sample 220. The interior surface area defined by the dashed line 230 thus indicates the location of the sealed volume or pocket 232 which will be formed upon abutting the o-ring 218 (FIG. 5C) against the lateral surface 222 of the test sample 220.

Figure 9:
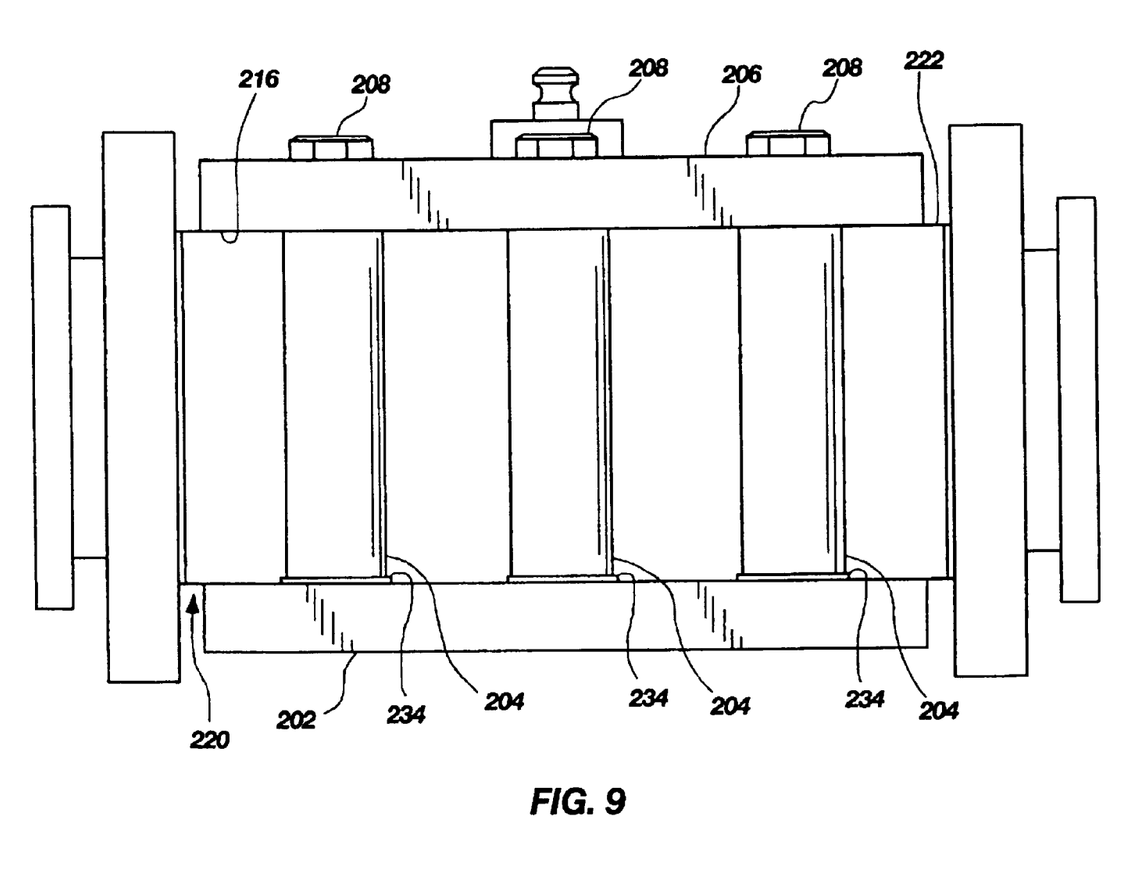
FIG. 9 is a side view of a material sample disposed in a testing apparatus and ready for testing in accordance with an embodiment of the present invention.

Referring to FIG. 9, the top plate 206 is positioned over the test sample 220 to form the sealed volume or pocket as indicated above. The fasteners 208 are used to couple the base plate 202, top plate 206 and spacers 204 as set forth above. Shims 234 or auxiliary spacers may be inserted, for example, between the spacers 204 and the base plate 202 to control the percent squeeze being applied between the o-ring 218 (FIG. 5C) and the lateral surface 222 of the test sample. When using an o-ring 218, percent squeeze may be defined as the original (uncompressed) diameter $D_o$ of the o-ring 218, minus the deformed or compressed diameter $D_c$ of the o-ring 218 after installation, divided by the original diameter $D_o$ multiplied by 100 as represented by Equation 1.

$$\frac{D_o - D_c}{D_o} \times 100 \qquad \text{Eq. 1}$$

Such control of the percent squeeze of the o-ring 218 may be desirable so that, for example, various types of seals or sealing configurations may be replicated or simulated. For example, in one embodiment, it may be desirable to induce an approximately 10–20 percent squeeze in the o-ring 218 to replicate a seal of a given configuration.

It is noted that the configuration of the testing apparatus 200 with the test sample 220 received thereby desirably enables a load to be applied to the test sample along a direction substantially perpendicular to its end surfaces 224 without substantial restriction of movement of the test sample 220 in that same direction. In other words, the test sample 220 may be allowed to deform (e.g., elongate) in the same direction as the applied force due to the configuration of the testing apparatus 200.

Figure 10:
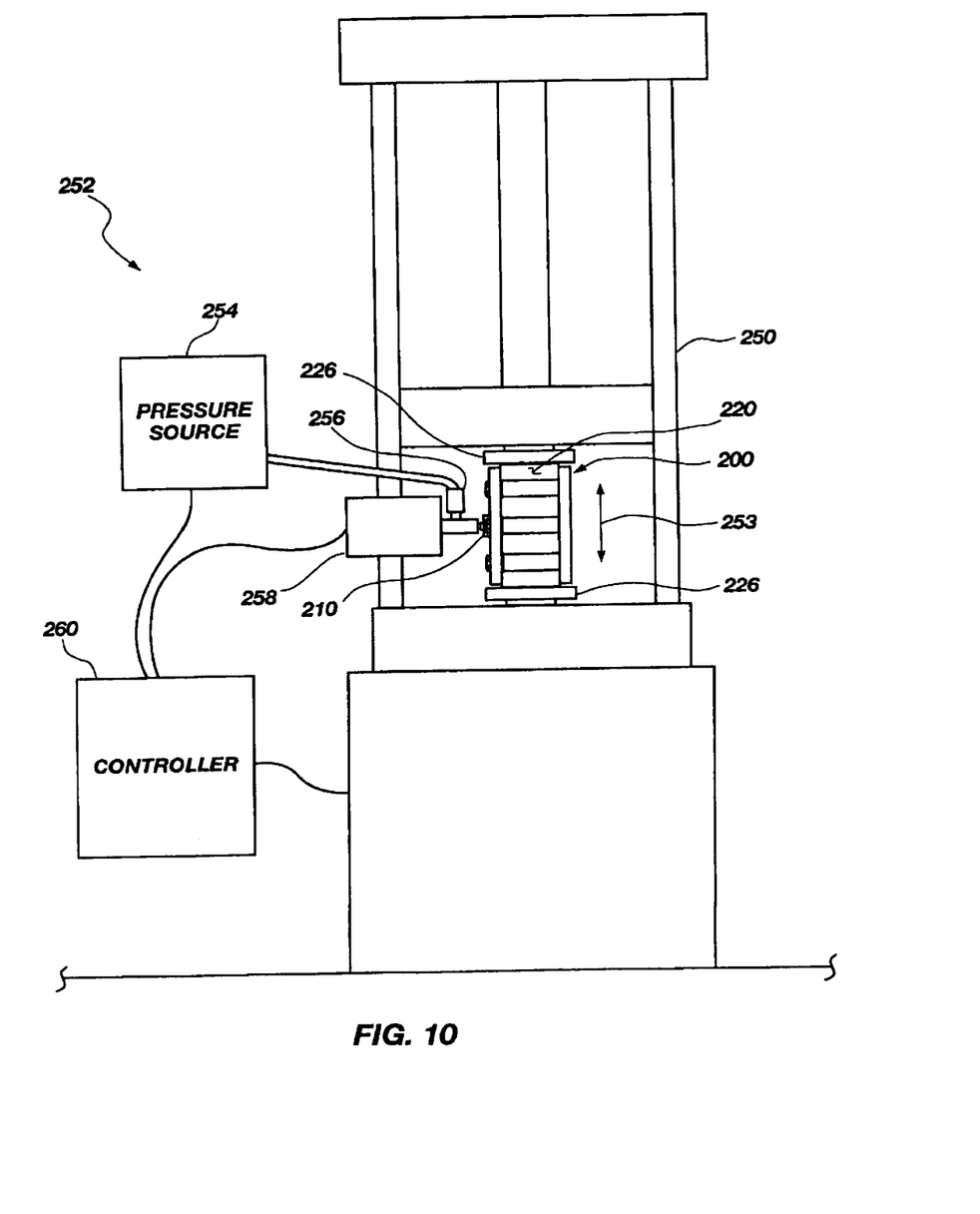
FIG. 10 shows a testing system incorporating the testing apparatus configured to test the material sample of FIG. 9 in accordance with another embodiment of the invention.

Referring now to FIG. 10, the test sample 220, installed in the test apparatus 200, may be operatively coupled with a load applying apparatus 250 of a testing system 252. The load applying apparatus may include, for example, a universal tester such as is commercially available from Instron Corporation of Canton, Mass. Such load applying apparatuses 250 may include various mechanical, electromechanical and/or hydraulic components configured to apply a load to a test sample engaged therewith at a specified magnitude. The exemplary load applying apparatus 250 is configured to apply a loading to the test sample 220 in the direction indicated by directional arrow 253.

A pressure source 254 may be coupled with the testing apparatus 200 by way of the port 210 to provide a desired amount of pressurized fluid in the sealed volume formed between a surface of the test sample 220 and the o-ring 218 (FIG. 5C). A valve 256, which may include, for example, a check valve, may be operatively coupled between the port 210 of the testing apparatus 200 and the pressure source 254. The pressure source may provide, for example, pressurized air or another gas from a pressurized tank or a compressor. In another embodiment, depending on the material being tested, the pressure source might provide a pressurize liquid rather than a gas.

The testing system 252 may further include a controller 260, which may include a processor-based computer or other programmable control unit. The controller 260 may be configured to control the magnitude of the load being applied by the load applying apparatus 250 and any desired rate of change of the load applied thereby. The controller 260 may also be configured to monitor the status of the test sample 220. The status of the test sample may include, for example, the length of time the test sample 220 has been under load, the loading conditions and the magnitude of deformation (e.g., elongation) experienced by the test sample 220 due to the applied load. The controller 260 may be further configured to control the pressure source 254 and/or valve 256.

A pressure transducer 258 or other sensor may be operatively coupled with the port 210 of the testing apparatus 200 or otherwise positioned and configured to monitor the pressure within the sealed volume formed between a surface of the test sample and the o-ring 218 (FIG. 5C). The pressure transducer 258 may also be coupled with the controller 260 such that the controller 260 may monitor the pressure within the defined sealed volume and maintain the pressure or otherwise alter the pressure in accordance with a specified testing routine.

It is noted that, while the exemplary embodiments described herein are described in terms of applying an across-ply load to a test specimen, that the testing system 252 and testing apparatus 200 may be configured to enable the application of other loadings and inducement of other stress rates. For example, in one embodiment, the test sample 220 may be configured to apply a loading in the same direction of the plies 221 of material (assuming a laminar test sample is being analyzed) rather than across the plies 221. In another embodiment, the test sample 220, testing apparatus 200 and testing system 252 may be configured such that a loading may be applied to the test sample to induced a shear stress between the individual plies 221.

EXAMPLE

Referring generally to the testing apparatus 200, test sample 220 and testing system 252 as shown and described with respect to FIGS. 4–10, a testing routine may be described regarding the determination of certain material properties of such a test sample 220. In one embodiment, test samples 220 were formed as laminar blocks including a plurality of plies of carbon cloth phenolic material. The test samples 220 exhibited a width W of approximately 1.700 inches with a tolerance of ±0.002 inches, a depth D of approximately 1.70 inches with a tolerance of ±0.01 inches, and a height H of 3.50 inches with a tolerance of +0.02 inches and and −0.00 inches. The end surfaces 224 were finished to approximately 100–200 Å Ra and the lateral surfaces 222 were finished to approximately 63 Å Ra. The test sample 220 was formed to exhibit a 63 Å Ra surface finish on an across-ply surface thereof. Actual dimensions of each test sample 220 were recorded.

The end surfaces 222 of the test samples 220 were bonded to fixtures 226 with TIGA-321 epoxy adhesive. Percent squeeze of the o-ring 218 was approximately 10 to 20 percent. Some of the test samples 220 were individually placed in the load applying apparatus 250 and an across-ply tensile load was applied to the test samples 220 thereby to establish a structural failure benchmark. A first test sample 220 failed at an applied load of between approximately 3,000 and 5,000 pounds (lbs) while the load applying apparatus 250 was steadily increasing the load in an effort to determine actual test sample 220 capability. The applied load of 3,000–5,000 lbs corresponds approximately to 1,038 to 1,730 pounds per square inch (psi) by taking into account the applied load and the cross-sectional area (W×D) of the test sample 220. A second test sample 220 failed at approximately 4,500 lbs (1557 psi). It is noted that the across-ply ultimate tensile strength of the carbon cloth phenolic test samples is rated at approximately 3,990 psi by Southern Research Institute (SRI) of Birmingham, Ala.

Other test samples 220 were individually placed in the testing apparatus 200 with the top plate 206 and the associated o-ring 218 being placed on a lateral surface 222 exhibiting a 63 Å Ra finish. The fasteners 208 were tightened using appropriate shims 234 so as to provide a desired amount of evenly applied pressure (i.e., a predetermined o-ring footprint) between the o-ring 218 and the lateral surface 222 of the test sample 220. The test sample 220 and testing apparatus 200 were installed into the load applying apparatus 250 and the fixtures 226 were operatively coupled therewith. The pressure source 254, valve 256 and pressure transducer 258 were operatively coupled with the port 210 of the testing apparatus 200 and a fluid was introduced into the sealed volume/pocket formed between the surface 222 and o-ring 218. The sealed volume was pressurized to approximately 80 psi and allowed to stabilize. An initial across-ply tensile load of approximately 1,500 lbs was applied to the test sample 220 by the load applying apparatus 250. The applied load was subsequently increased at intervals of approximately 500 lbs. The loads were maintained at each interval for approximately 15 to 20 minutes in order to stabilize pressure conditions within the sealed volume.

Figure 11:
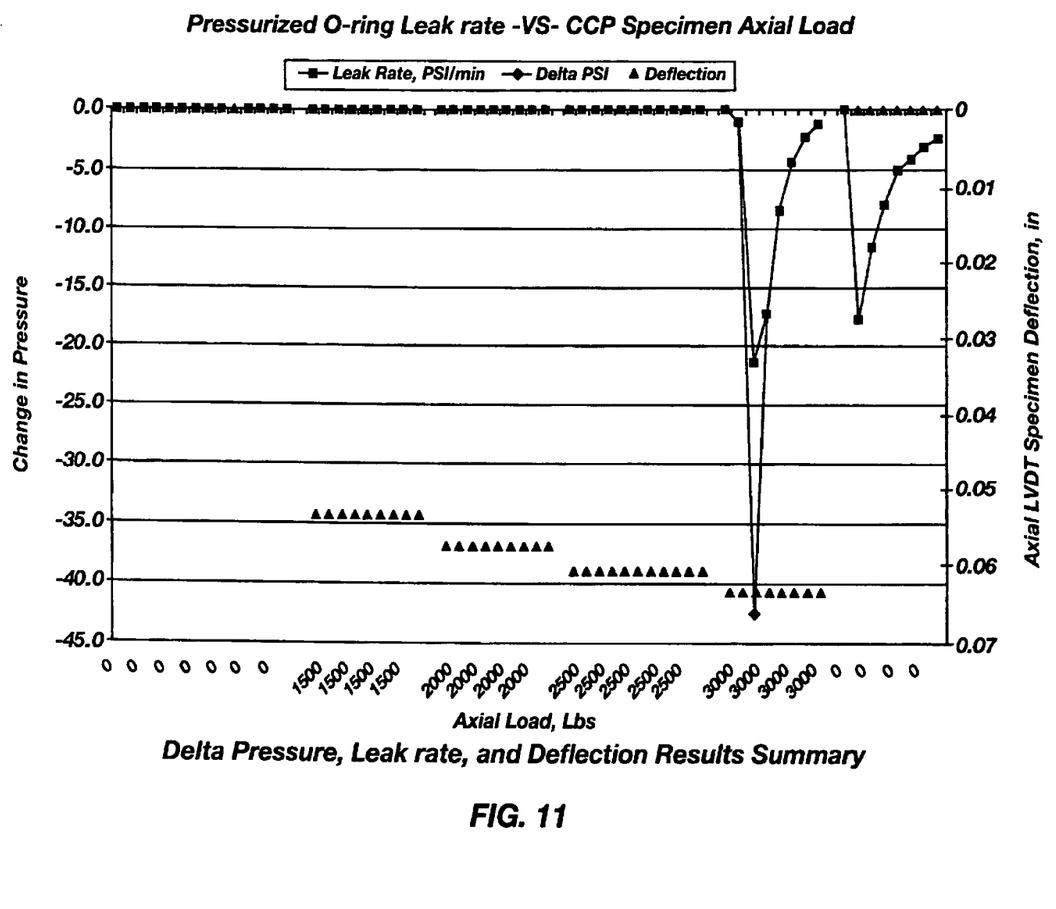
FIG. 11 is a graph related to the implementation of the present invention in accordance with one embodiment thereof.

Referring to the graph of FIG. 11, it can be seen that, at an across-ply applied load of approximately 3,000 lbs (1,038 psi), the test sample 220 experienced a deflection of greater than approximately 0.06 inches and a pressure loss of more than 40 psi from the sealed volume defined between the o-ring 218 and the surface 222 of the test sample 220. The applied load was then removed from the test sample 220 and an attempt was made to reestablish the pressure of the sealed volume to approximately 80 psi. However, subsequent the initial loss of pressure from the sealed volume, a pressure loss of more than approximately 15 psi was experienced from the sealed volume without any across-ply applied load to the test sample 220 indicating permanent defects in the surface 222 of the test sample which were sufficient to prevent the reestablishment of an effective seal between the o-ring 218 and the surface 222 of the test sample 220.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method of testing surface characteristics of a material, the method comprising:
    providing a body comprising a material to be tested;
    defining a sealed volume, a portion of the sealed volume including a surface of the body;
    supplying a pressurized fluid to the sealed volume;
    applying a load to the body including increasing a magnitude of the load at a predetermined rate;
    monitoring the sealed volume for indications of a loss of the pressurized fluid; and determining the magnitude of the load upon detection of the loss of pressurized fluid.

2. The method according to claim 1, wherein providing a body includes forming a body of a composite material.

3. The method according to claim 2, wherein forming a body of a composite material further comprises forming a body of a material comprising at least one of a carbon cloth phenolic material, a glass cloth phenolic material, a silica cloth phenolic material and a carbon-carbon material.

4. The method according to claim 2, wherein providing a body further includes forming a laminar structure of the composite material.

5. The method according to claim 1, wherein defining a sealed volume includes providing a structure adjacent the surface of the body, and disposing a sealing member between and in sealing communication with the body and a surface of the structure.

6. The method according to claim 5, wherein supplying a pressurized fluid to the sealed volume further comprises forming a passage through the structure, configuring a first end of the passage to be in communication with the sealed volume and coupling a second end of the passage with a pressurized fluid source.

7. The method according to claim 6, wherein supplying a pressurized fluid to the sealed volume further comprises disposing a valve between the pressurized fluid source and the sealed volume.

8. The method according to claim 5, wherein disposing a sealing member between and in sealing communication with the body and a surface of the structure includes disposing an o-ring between the body and the surface of the structure.

9. The method according to claim 8, wherein disposing an o-ring between the body and the surface of the structure further includes at least partially disposing the o-ring in a circuitous channel formed in the surface of the structure.

10. The method according to claim 8, further comprising applying a compressive force to the o-ring between the body and the surface of the structure.

11. The method according to claim 10, further comprising substantially equally distributing the compressive force throughout the o-ring.

12. A method of testing surface characteristics of a material, the method comprising:
    providing a body comprising a laminar structure of composite material to be tested, the composite material comprising at least one of a carbon cloth phenolic material, a glass cloth phenolic material, a silica cloth phenolic material and a carbon-carbon material;
    defining a sealed volume, a portion of the sealed volume including a surface of the body;
    supplying a pressurized fluid to the sealed volume;
    applying a load to the body;
    monitoring the sealed volume for indications of a loss of the pressurized fluid; and
    orienting plies of the laminar structure to exhibit a specified ply angle relative to the surface of the body used to define the sealed volume.

13. The method according to claim 12, wherein applying a load to the body further includes applying an across-ply tensile load to the body.

14. The method according to claim 12, wherein applying a load to the body further includes inducing a tensile stress in at least a portion of the surface of the body used to define the sealed volume.

15. The method according to claim 14, wherein applying a load to the body further includes applying the load at an initial level and maintaining the load for a defined period of time.

16. The method according to claim 15, wherein applying a load to the body further includes repeatedly increasing the load by a defined load interval and, after each increase, maintaining the load as increased for the defined period of time.

17. The method according to claim 16, wherein monitoring the sealed volume for indications of a loss of the pressurized fluid includes monitoring a pressure of the sealed volume.

18. The method according to claim 17, wherein monitoring a pressure of the sealed volume further includes detecting a change in pressure of the sealed volume upon an increase of loading.

19. The method according to claim 18, further comprising substantially releasing the applied load upon the detection of the change of pressure of a predetermined level.

20. The method according to claim 19, further comprising supplying additional pressurized fluid to the sealed volume and further monitoring the sealed volume for further indications of a loss of the pressurized fluid.

21. A testing fixture comprising:
    a first support member;
    a second support member;
    a plurality of spacers disposed between the first support member and second support member and defining a volume for receipt of a material test sample between the first support member and second support member;
    a circuitous seal member disposed against a surface of the second support member and located and configured to be disposed against a surface of the material test sample;

a port in fluid communication with an interior area defined by the circuitous seal member; and a plurality of fasteners configured to couple the first support member, the second support member and the plurality of spacers with one another.

22. The testing apparatus of claim 21, wherein the plurality of spacers includes at least one spacer disposed adjacent a first side of the volume and at least one spacer disposed on a second opposing side of the volume.

23. The testing apparatus of claim 21, wherein the second support member includes a passage defined therethrough and wherein a first end of the passage is in fluid communication with the interior area defined by the circuitous seal member and a second end in fluid communication with the port.

24. The testing apparatus of claim 23, wherein the port is configured to be coupled with a source of pressurized fluid.

25. The testing apparatus of claim 24, further comprising a pressure transducer in fluid communication with the passage.

26. The testing apparatus of claim 23, further comprising a channel defined in the surface of the second support member and wherein the circuitous seal member is at least partially disposed within the channel.

27. The testing apparatus of claim 26, wherein the circuitous seal member includes an o-ring.

28. The testing apparatus of claim 27, further comprising at least one shim disposed between at least one spacer of the plurality of spacers and at least one of the first support member and the second support member.

29. A testing fixture comprising:

a first support member;

a second support member;

a plurality of spacers disposed between the first support member and second support member and defining a volume for receipt of a material test sample between the first support member and second support member;

a circuitous seal member disposed against a surface of the second support member and located and configured to be disposed against a surface of the material test sample;

a port in fluid communication with an interior area defined by the circuitous seal member;

a first fixture configured to be bonded to a first end of the material test sample; and a second fixture configured to be bonded to a second end of the material test sample, wherein the first fixture and second fixture are each further configured to be operatively coupled with a load applying apparatus.

30. A system comprising:

a testing fixture comprising:

a first support member;

a second support member;

a plurality of spacers disposed between the first support member and second support member and defining a volume for receipt of a material test sample between the first support member and second support member;

a seal member disposed against a surface of the second support member and against a surface of the material test sample thereby forming a sealed volume between the second support member and the surface of the material test sample; and a plurality of fasteners configured to couple the first support member, the second support member and the plurality of spacers with one another;

a source of pressurized fluid in fluid communication with the sealed volume; and a load applying apparatus configured to apply a defined load to the material test sample.

31. The system of claim 30, wherein the material test sample is formed of a material comprising at least one of a carbon cloth phenolic material, a glass cloth phenolic material, silica cloth phenolic material and a carbon-carbon material.

32. The system of claim 30, further comprising a controller operably coupled with the load applying apparatus and configured to control the magnitude of the load applied thereby to the material test sample.

33. The system of claim 32, further comprising a pressure transducer in communication with the sealed volume and configured to monitor a pressure of any fluid disposed within the sealed volume.

34. The system claim 33, wherein the controller is further configured to control the pressure of any fluid disposed within the sealed volume.

35. The system of claim 34, further comprising a valve in fluid communication with the sealed volume and operatively coupled with the source of pressurized fluid.

36. The system of claim 30, wherein the plurality of spacers includes at least one spacer disposed adjacent a first side of the material test sample and at least one spacer disposed on a second opposing side of the material test sample.

37. The system of claim 30, wherein the second support member includes a passage defined therethrough and wherein a first end of the passage is in communication with the sealed volume and a second end in communication with the source of pressurized fluid.

38. The system of claim 37, wherein the port is configured to be coupled with a source of pressurized fluid.

39. The system of claim 38, further comprising a pressure transducer in fluid communication with the passage.

40. The system of claim 37, further comprising a channel defined in the surface of the second support member and wherein the circuitous seal member is at least partially disposed within the channel.

41. The system of claim 40, wherein the circuitous seal member includes an o-ring.

42. The system of claim 41, further comprising at least one shim disposed between at least one spacer of the plurality of spacers and at least one of the first support member and the second support member.

43. A system comprising:

a testing fixture comprising:

a first support member;

a second support member;

a plurality of spacers disposed between the first support member and second support member and defining a volume for receipt of a material test sample between the first support member and second support member; and a seal member disposed against a surface of the second support member and against a surface of the material test sample thereby forming a sealed volume between the second support member and the surface of the material test sample;

a source of pressurized fluid in fluid communication with the sealed volume; and a load applying apparatus configured to apply a defined load to the material test sample;

a first fixture bonded to a first end of the material test sample; and a second fixture configured to be bonded to a second end of the material test sample, wherein the first fixture and second fixture are each further configured to be operatively coupled with the load applying apparatus.

44. The system of claim 43, wherein the material test sample is formed of a composite material.

45. The system of claim 44, wherein the material test sample is formed as laminar structure including a plurality of plies of the composite material.

46. The system of claim 45, wherein the plurality of plies are configured and oriented such that the load applying apparatus induces an across-ply load to the material test sample.

* * * * *

UNITED STATES PATENT AND TRADEMARK OFFICE
CERTIFICATE OF CORRECTION

PATENT NO. : 7,040,143 B2 Page 1 of 1
APPLICATION NO. : 10/651311
DATED : May 9, 2006
INVENTOR(S) : David L. Johnson et al.

It is certified that error appears in the above-identified patent and that said Letters Patent is hereby corrected as shown below:

| | | |
|---|---|---|
| COLUMN 3, | LINE 63, | after "plurality" and before "CCP" insert --of-- |
| COLUMN 8, | LINE 8, | change "induced" to --induce-- |
| COLUMN 8, | LINE 21, | delete first occurrence of "and" |

Signed and Sealed this

Third Day of March, 2009

JOHN DOLL
*Acting Director of the United States Patent and Trademark Office*